(12) United States Patent
Furuta

(10) Patent No.: US 7,060,974 B2
(45) Date of Patent: *Jun. 13, 2006

(54) LASER DESORPTION IONIZATION MASS SPECTROMETRIC METHOD AND SAMPLE PLATE USED IN SUCH A METHOD

(75) Inventor: Masaru Furuta, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 92 days.

This patent is subject to a terminal disclaimer.

(21) Appl. No.: 10/699,821

(22) Filed: Nov. 4, 2003

(65) Prior Publication Data

US 2004/0094708 A1    May 20, 2004

(30) Foreign Application Priority Data

Nov. 11, 2002    (JP) ............................. 2002-326655

(51) Int. Cl.
*H01J 49/04*    (2006.01)
(52) U.S. Cl. .................. 250/288 H; 250/281; 250/282; 435/6
(58) Field of Classification Search ................ 250/288, 250/281, 282; 435/6; 436/173
See application file for complete search history.

(56) References Cited

U.S. PATENT DOCUMENTS

| | | | |
|---|---|---|---|
| 4,527,059 A | * | 7/1985 | Benninghoven et al. .... 250/288 |
| 5,595,636 A | * | 1/1997 | Franzen ....................... 204/464 |
| 5,808,300 A | * | 9/1998 | Caprioli ....................... 250/288 |
| 6,423,966 B1 | * | 7/2002 | Hillenkamp et al. ........ 250/288 |
| 6,831,270 B1 | * | 12/2004 | Furuta et al. ................ 250/281 |
| 2003/0096426 A1 | * | 5/2003 | Little et al. .................. 436/173 |

FOREIGN PATENT DOCUMENTS

JP    10-040858 A1    2/1998
WO    WO-98/47006 A1    10/1998

* cited by examiner

*Primary Examiner*—Nikita Wells
*Assistant Examiner*—Zia R. Hashmi
(74) *Attorney, Agent, or Firm*—Rader, Fishman & Grauer, PLLC

(57) ABSTRACT

The present invention relates to a sample plate that is preferably constituted by a metal plate on which a membrane is affixed by a conductive double-sided tape. In the case where a sample, developed on a medium such as an electrophoresis gel, is transferred onto the membrane, in the same manner as a conventional blotting operation, a medium such as gel and the sample plate are sandwiched between flat plate electrodes so that the medium and the membrane are made in closely contact with each other, and a voltage is applied between both of the electrodes. Thus, the sample developed on the medium is transferred on the membrane through electrophoresis. Upon laser desorption ionization mass spectrometry, the sample plate is compatibly used as a plate for mass spectrometry.

14 Claims, 2 Drawing Sheets

LASER DESORPTION IONIZATION MASS SPECTROMETRIC METHOD AND SAMPLE PLATE USED IN SUCH A METHOD

BACKGROUND OF THE INVENTION

1. Field of the Invention

The present invention relates to a method for analyzing a substance that has been developed over a membrane in a solid phase by using a laser desorption ionization mass spectrometric method and a sample plate used in such a method, in various fields such as clinical, diagnostic, biochemical and molecular biological fields.

2. Description of the Background Art

In order to analyze a mass of molecules to be measured, a laser desorption ionization mass spectrometric method has been used in which a laser beam is applied to a sample placed on a sample plate attached to a mass spectrometer so that the sample is ionized and analyzed (see JP-A No. 10-40858). Upon placing the sample on the sample plate so as to be analyzed, there are two methods, that is, one method in which a matrix is used and the other method in which a matrix is not used.

A method in which the method using a matrix is combined with a time-of-flight mass spectrometer is referred to as MALDI-TOF (matrix-assisted laser desorption ionization time-of-flight) mass spectrometric method.

The MALDI-TOF mass spectrometric method is a technique capable of analyzing molecules ranging from a low molecular weight to a high molecular weight, quickly with high sensitivity. In particular, this method exerts superior capabilities in analyzing biological samples such as proteins, peptides and nucleic acid molecules.

In the case where a measuring sample is given as a mixture, with respect to the sample, normally, molecules to be measured are selected in a separated state through gel electrophoresis, and after being extracted from the gel through various reactions, the sample is placed on a metal sample plate together with a matrix solution.

Here, with respect to the measuring sample, a mass spectrometric method has been proposed in which after biomolecules have been separated through electrophoresis or the like, these are transferred onto a membrane in a solid phase, and the solid-phase sample is subjected to various reactions on the membrane by utilizing a trace-amount application technique using a piezoelectric element, and the resulting reaction products are utilized to carry out mass analysis (see International Publication No. WO98/47006).

In order to achieve a system in which the sample, separated through gel electrophoresis, is transferred onto a membrane, subjected to a reaction by applying trace amounts of various reagents thereto, and introduced into a mass spectrometer, complex operations are required in respective steps or transit states between the steps. In other words, the respective operations are independent individually, and no systematic compatibility is prepared for these operations. For this reason, the membrane bearing the solid-phase sample is removed from the transferring device, and shifted to a stage for trace-amount application processes, and then fixed onto a sample plate for mass spectrometry; therefore, the supporting members for the membrane need to be changed in the respective stages.

The above explanation has exemplified a case in which the sample for use in MALDI-TOF measurements is prepared. However, the same problem arises also in the case where the sample is prepared without using a matrix.

SUMMARY OF THE INVENTION

An object of the present invention is to unify the supporting member of a membrane with respect to cases with or without a matrix, and consequently to achieve labor-saving in a sequence of operations for preparing the sample.

In order to achieve the above-mentioned objective, the present invention preliminarily prepares a metal plate on which a membrane is affixed so as to eliminate the necessity of changing membrane supporting members in a sequence of operations including a sample transferring process from gel, application process of a reagent, a reaction process and mass spectrometry.

In other words, the laser desorption ionization mass spectrometric method of the present invention is provided with the steps of: adsorbing a sample on a membrane which has been affixed beforehand on a flat metal plate of the sample plate; applying a reagent to the adsorbed sample on the membrane so as to subject the sample to a modifying reaction, and analyzing the sample through a laser desorption ionization mass spectrometric method by attaching the sample plate to a mass spectrometer after the modifying reaction.

The sample plate of the present invention is used for a laser desorption ionization mass spectrometric method, and formed by preliminarily affixing a membrane onto a flat metal plate.

In this manner, the membrane, preliminarily affixed onto the metal plate, need not be replaced by another member, and the metal plate is allowed to function as an electrode upon transferring the sample from gel, as a sample holding stage upon applying a reagent or a matrix solution, and also as a sample plate upon mass spectrometry.

One of the preferable methods for the ionization of the sample is a matrix-assisted laser desorption ionization method. In this case, prior to attaching the sample plate to the mass spectrometer after the above-mentioned modifying reaction, a step for applying a matrix solution to the sample is further prepared.

One of the preferable examples for the adsorbing step of the sample to the membrane is a method in which a medium on which the sample is developed is superposed on the membrane on a sample plate and a voltage is applied between the medium and the membrane so that the sample is transferred onto the membrane from the medium.

One of the preferable examples for the sample plate is a metal plate having a homogeneous flat face on which a membrane is made closely in contact with the homogeneous flat face of the metal plate with a conductive substance interpolated in between, and affixed thereon.

Examples of the sample to be adsorbed on the membrane include molecules of proteins, peptides, saccharides, lipids, nucleic acid molecules and the like or a mixture of these molecules that are separated through SDS (sodium dodecyl sulfate) polyacrylamide electrophoresis, two-dimensional electrophoresis in which isoelectric focusing electrophoresis and SDS polyacrylamide electrophoresis are combined, or other chromatography processes.

These samples may be modified by a proteolytic enzyme, a glycolytic enzyme, nuclease or a combination thereof.

With respect to the material of a membrane to be used for adsorbing a sample, examples thereof include PVDF (polyvinylidene difluoride), nitrocellulose, nylon (registered trademark) or derivatives thereof.

The sample that is adsorbed on the membrane may be visualized on the membrane by using another bio-sample, a color-developing reagent, a phosphorous reagent, metal, ultraviolet rays or a combination of these.

With respect to the handling of a membrane used for adsorbing the sample by a conventional blotting method, time-consuming processes including complex operations are required, since the membrane is fragile and susceptible to damage and since special techniques are required so as to make the membrane closely in contact with a supporting member without containing bubbles and the like in each of the steps. In the present invention, the membrane has been closely made in contact with a metal plate and affixed thereon all the time; therefore, it is possible to achieve labor-saving to a great degree in a sequence of processes including the sample transferring process from the gel or the like, application process of a reagent or a matrix and mass spectrometry.

DESCRIPTION OF THE PREFERRED EMBODIMENT

Figure 1A:
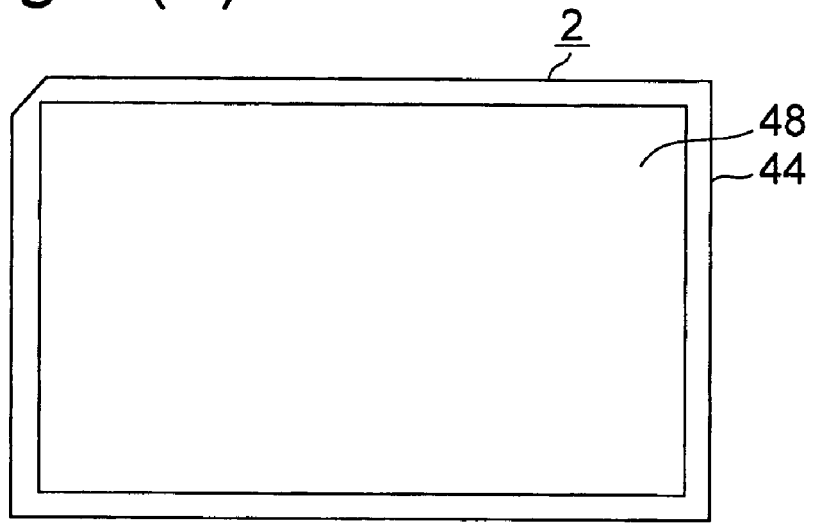
FIG. 1(A) is a plan view that shows a sample plate in accordance with one embodiment.
Figure 1B:
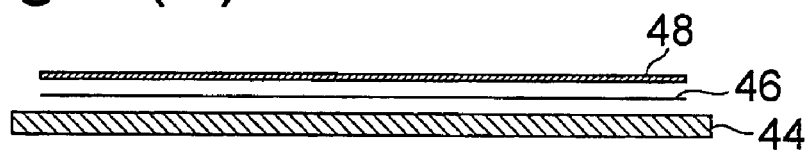
FIG. 1(B) is an exploded cross-sectional view that shows a lateral cross-section of the sample plate of FIG. 1(A).

FIGS. 1(A) and 1(B) show a sample plate 2 of one embodiment FIG. 1(A) is a plan view thereof, and FIG. 1(B) is an exploded cross-sectional view that shows a lateral cross-section of the sample plate of FIG. 1(A).

The sample plate 2 is constituted by a metal plate 44 and a membrane 48 that is affixed thereto in a conductive state.

With respect to the metal plate 44, a stainless plate is used, and the surface on which the membrane 48 is affixed forms a homogeneous flat face so that the membrane 48 is closely made in contact therewith. With respect to the affixing process of the membrane 48, for example, a conductive double-sided tape 46 is used.

The sample plate 2 is compatibly used as a plate for mass spectrometry.

Figure 2:
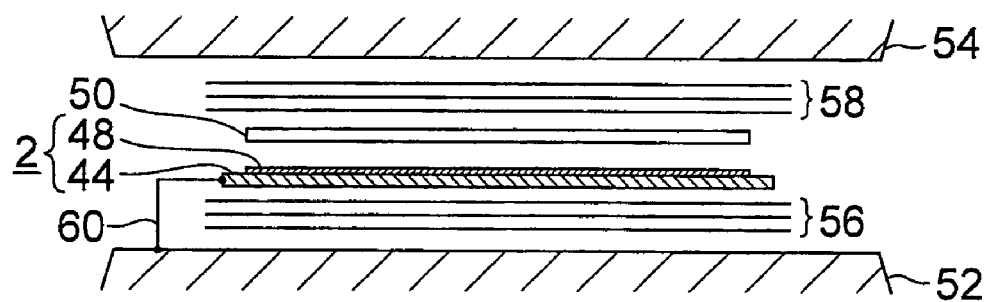
FIG. 2 is an exploded cross-sectional view that shows a blotting process in which the sample plate of the embodiment is used.

When a sample, developed on a medium such as an electrophoresis gel, is transferred onto the membrane 48, the same processes as those of a conventional blotting operation are carried out. FIG. 2 shows the state of the operation. A medium 50 such as gel and the sample plate 2 are sandwiched between flat plate electrodes 52 and 54 so that the medium 50 and the membrane 48 are made in closely contact with each other. In this case, in order to make the flat plate electrodes 52, 54 of a blotting device and the metal plate 44 in closely contact with each other and to hold an electrolytic solution during the transferring process, a plurality of sheets of filter paper 56 or the like, moistened with the solution, are superposed on one another, and sandwiched between the flat plate electrode 52 and the metal plate 44, and filter paper 58 or the like is sandwiched between the flat plate electrode 54 and the medium 50.

During the blotting operation, the metal plate 44 and the flat plate electrode 52 are connected to each other with a wire 60 so as to be set to the same potential, and a voltage is applied between both of the electrodes 52 and 54 so that the flat plate electrode 52 is set to plus, with the flat plate electrode 54 being set to minus. Thus, the sample, developed in the medium 50, is transferred onto the membrane 48 through electrophoresis.

The sample, prepared by using the sample plate of the present invention, is analyzed by a laser desorption ionization mass spectrometer. The laser desorption ionization mass spectrometer is provided with an ionization chamber in which only the sample or a mixture of the sample and a matrix is placed as an analyzing object, a laser irradiation optical system which ionizes the sample by applying laser light to the analyzing object, and a mass spectrometry unit which extracts and separates the ionized sample ions, and analyzes the ions in accordance with mass number. In the laser desorption ionization mass spectrometer, a laser beam, such as a nitrogen gas laser (wavelength: 337 nm), an Nd-YAG laser (wavelength: 266 nm or 355 nm) and a carbon dioxide gas laser (wavelength: 1060 nm, 2.94 µm), is applied to the analyzing object so that the sample is ionized, and the ionized sample is directed to the mass spectrometry unit, and analyzed therein. This analyzing method makes it possible to converge the laser light to a diameter of as small as several µm; therefore, public attention has been focused on this method with respect to its capability of analyzing a minute portion.

In the case where the analyzing object is limited to only the sample, the sample itself absorbs the laser light to directly obtain energy from the laser light, and is ionized. In the case where a matrix is used, the matrix absorbs the laser light to convert it to thermal energy, and one portion of the matrix is rapidly heated to evaporate together with the sample. In this case, even when the sample molecules are desorbed in the neutral state, if protons or cations (that exist as impurities) that are simultaneously evaporated or matrix ions are added to the sample molecules, sample ions are formed. The laser beam is preferably applied as a pulse laser beam of approximately 1 nano second.

With respect to the sample preparation in the case of using a matrix, after mixing a sample solution and a matrix solution at a molar ratio of 1:100 to 1:10000, the resulting mixture is dried to obtain a state in which both of the solutions are uniformly mixed in the level of micron. As a result, a crystalline state or an amorphous state in which fine crystals of the sample are surrounded by a great amount of matrix crystals is formed. In general, this analyzing object contains cations or anions which are preliminarily added or impurities.

With respect to the mass spectrometry unit used for laser desorption ionization mass spectrometry, a time-of-flight mass spectrometer (TOFMS) is used; however, other spectrometers, such as a Fourier transform-type ion cyclotron resonance mass spectrometer (FTMS), a double convergence-type mass spectrometer (double focus MS) which selects ions and directs the resulting ions to the detector by using a magnetic field and an electric field, a three dimensional quadruple-pole type ion trap mass spectrometer or the like, may also be used.

In the case where the laser desorption ionization and the time-of-flight mass spectrometer are combined with each other, with respect to the molecular weight, even immunoglobulin M (average molecular weight: 900 kDa) can be detected, and it is said that the detection limit has reached the amol level. The compounds that can be ionized include a wide range of compounds such as general bio-related substances including peptides, proteins, polysaccharides, complex lipids and nucleic acid related substances, synthetic polymers, oligomers, metal coordination compounds and inorganic compounds.

In the case where a matrix is used, various kinds of matrixes can be used, and examples thereof include nicotinic acid, 2-pyrazine carboxylic acid, sinapic acid, 2,5-dihydroxy benzoic acid, 5-methoxy salicylic acid, α-cyano-4-hydroxy cinnamic acid, 3-hydroxy picolic acid, diamino naphthalene, 2-(4-hydroxyphenylazo) benzoic acid, dithranol, succinic acid, 5-(trifluoromethyl) uracil and glycerin (see "Bunseki" No. 4, pp. 253 to 261 (1996)).

Figure 3:
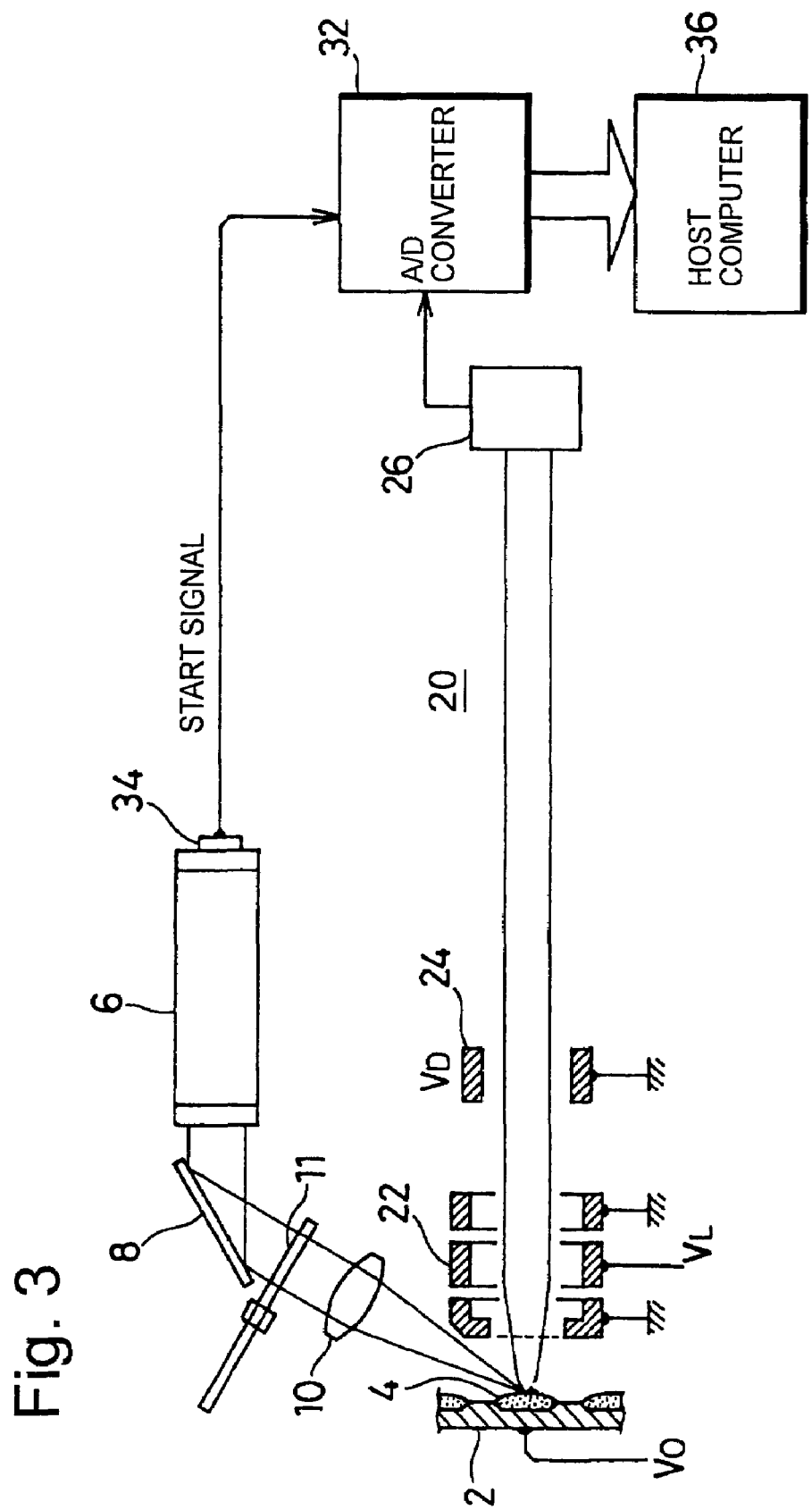
FIG. 3 is a schematic structural drawing that shows one example of an MALDI-TOF mass spectrometer.

FIG. 3 shows one example of the MALDI-TOF mass spectrometer.

An analyzing object 4, placed on a sample plate 2, is put in an ionization chamber. In this case, it is supposed that the analyzing object 4 is a mixture of a sample and a matrix. In order to converge a laser beam from a nitrogen laser (wavelength: 337 nm) 6 used for ionizing the sample onto the analyzing object 4 so as to be irradiated, a mirror 8, an optical lens 10 which converges a laser beam that is bent by the mirror 8 and an optical filter 11 that eliminates unnecessary high harmonic waves and the like of the laser light are installed.

A time-of-flight mass spectrometer is installed as a mass spectrometry unit for analyzing the sample ions that have been subjected to an ionizing process. The mass spectrometer is provided with an ion lens 22 that approaches the analyzing object 4 so as to extract ions, a deflection plate 24 which directs the ions extracted through the ion lens 22 toward the detector or in a direction deviated from the direction of the detector, and a detector 26 on which the ions that have passed through the deflection plate 24 are made incident and detected.

An ion detection signal, outputted from the detector 26, is directed to an AD converter 32. In the time-of-flight mass spectrometer, in order to determine the origin (zero point) of time from which time-of-flight is measured, a photodiode 34 is placed in the nitrogen laser 6, and a detection signal of the photodiode 34 is directed to the AD converter 32 as a start signal. The AD converter 32 converts the signal from the detector 26 to a digital signal by using the start signal as the origin of time. Reference numeral 36 represents a host computer which receives the detector signal converted to the digital signal by the AD converter 32, and carries out data processing thereon, as well as controlling the operations of the entire spectrometer.

Next, the following description will discuss the operations of this MALDI-TOF mass spectrometer.

A laser beam is adjusted by a filter 11, converged by the lens 10, and applied to the analyzing object 4 so as to be ionized. The sample ions, thus generated, are extracted by a voltage Vo applied to the sample plate 2 and a ground potential on the analyzing object side of the ion lens 22, and the extracted ions are allowed to fly in a parallel path by a voltage VL applied to the ion lens located on the next stage. When the potential VD of the deflection plate 24 is set to the ground potential, the ions are allowed to linearly fly to reach the detector 26 and detected thereby.

When a potential VD is applied to the deflection plate 24, the ion flow is bent, and no longer reaches the detector 26.

After having been detected and amplified by the detector 26, the ions are converted to digital signals by the AD converter 32 with the laser oscillation time point serving as the time-of-flight origin, and directed to the host computer 36 so as to be analyzed.

The laser 6 is installed at an external portion of a vacuum system of the analyzing unit 20, and the laser beam is introduced through a light-introducing window of the vacuum system.

What is claimed is:

1. A laser desorption ionization mass spectrometric method, which applies a laser beam to a sample placed on a sample plate attached to a mass spectrometer so that the sample is ionized and then analyzed, comprising the steps of:
   adsorbing a sample on a membrane which has been affixed on a flat metal plate of the sample plate;
   applying a reagent to the adsorbed sample on the membrane to subject the sample to a modifying reaction; and
   analyzing the sample through a laser desorption ionization mass spectrometric method by attaching the sample plate after the modifying reaction to a mass spectrometer.

2. The laser desorption ionization mass spectrometric method according to claim 1, further comprising the step of;
   prior to attaching the sample plate to the mass spectrometer after the modifying reaction, applying a matrix solution to the adsorbed sample,
   wherein, in the analyzing step, the ionizing process is carried out through a matrix-assisted laser desorption ionization method.

3. The laser desorption ionization mass spectrometric method according to claim 1, wherein the adsorbing step of the sample onto the membrane is carried out through a method in which a medium on which the sample is developed is superposed on the membrane on the sample plate and a voltage is applied between the medium and the membrane so that the sample is transferred onto the membrane from the medium.

4. The laser desorption ionization mass spectrometric method according to claim 1, wherein the sample to be adsorbed on the membrane is at least a material selected from the group consisting of proteins, peptides, saccharides, lipids, nucleic acid molecules and a mixture thereof.

5. The laser desorption ionization mass spectrometric method according to claim 4, wherein the sample is separated by a method selected from the group consisting of two-dimensional electrophoresis in which isoelectric focusing electrophoresis and SDS polyacrylamide electrophoresis are combined, SDS polyacrylamide electrophoresis and other chromatography methods.

6. The laser desorption ionization mass spectrometric method according to claim 1, wherein the modifying reaction is a reaction caused by an enzyme selected from the group consisting of proteolytic enzyme, glycolytic enzyme, nuclease and a combination thereof.

7. The laser desorption ionization mass spectrometric method according to claim 1, wherein the membrane is at least a polymer selected from the group consisting of PVDF, nitrocellulose, nylon (registered trademark) and derivatives thereof.

8. The laser desorption ionization mass spectrometric method according to claim 1, wherein the sample adsorbed on the membrane is visualized on the membrane.

9. The laser desorption ionization mass spectrometric method according to claim 8, wherein the visualizing process is carried out by using at least a material selected from the group consisting of a bio-sample, a color-developing reagent, a fluorescence reagent, metal, ultraviolet rays and a combination thereof.

10. A sample plate comprising:
    a flat metal plate having a flat surface; and
    a membrane being affixed onto the flat surface of the flat metal plate.

11. The sample plate according to claim 10, wherein the metal plate has a homogeneous flat face and the membrane is closely made in contact with the flat face of the metal plate to be affixed thereon with a conductive substance interpolated in between.

12. The sample plate according to claim 11, wherein the conductive substance is a conductive double-sided tape.

13. The sample plate according to claim 10, wherein the membrane is at least a polymer selected from the group consisting of PVDF, nitrocellulose, nylon (registered trademark) and derivatives thereof.

14. The sample plate according to claim 10, wherein the sample plate is compatibly used as a plate used for mass spectrometry.

* * * * *